(12) United States Patent
Murphy et al.

(10) Patent No.: US 9,107,409 B2
(45) Date of Patent: *Aug. 18, 2015

(54) PHYSICAL MODE OF ACTION PESTICIDE

(71) Applicant: Cal Agri Products, LLC, Los Angeles, CA (US)

(72) Inventors: Brook Chandler Murphy, Davis, CA (US); Todd C. Steckler, Oceanside, NY (US)

(73) Assignee: Cal Agri Products, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/628,625

(22) Filed: Sep. 27, 2012

(65) Prior Publication Data

US 2013/0022636 A1 Jan. 24, 2013

Related U.S. Application Data

(63) Continuation of application No. 12/500,051, filed on Jul. 9, 2009, now Pat. No. 8,298,559, which is a continuation of application No. 10/463,955, filed on Jun. 18, 2003, now Pat. No. 7,579,017.

(51) Int. Cl.
*A01N 25/32* (2006.01)
*A01N 43/16* (2006.01)
(Continued)

(52) U.S. Cl.
CPC ............ *A01N 43/16* (2013.01); *A01N 63/02* (2013.01); *A01N 65/00* (2013.01); *A01N 65/03* (2013.01)

(58) Field of Classification Search
CPC ..... A01N 25/32; A01N 25/006; A01N 25/04; A01N 25/22; A01N 25/30; A01N 31/04; A01N 31/14; A01N 37/02; A01N 43/04; A01N 43/08; A01N 43/16; A01N 59/26; A01N 65/03; A01N 65/00
USPC ............... 424/405, 406, 195.17, 195.18, 407, 424/601, 780
See application file for complete search history.

(56) References Cited

U.S. PATENT DOCUMENTS 4,227,911 A 10/1980 Leonard et al.
4,764,529 A * 8/1988 Naik et al. .................... 514/531
(Continued)

FOREIGN PATENT DOCUMENTS

JP 03261701 * 11/1991
WO 2008/094378 8/2008

OTHER PUBLICATIONS

Brazilian Office Action for Patent Application PI0411500-7, mailed on May 21, 2014, 10 pages.
(Continued)

*Primary Examiner* — Jeffrey T Palenik
(74) *Attorney, Agent, or Firm* — Kilpatrick Townsend & Stockton LLP

(57) ABSTRACT

A physical mode of action pesticide for application on plants and in soils, and methods of manufacture and application, comprising an active ingredient in the form of a polymer in a concentration of less than 0.1% wt., a surfactant, a co-solvent and a diluent in a hydrocolloid suspension. The suspension polymer is preferably a polysaccharide having a molecular weight of 10,000 to 25,000,000, and preferably in the range of about 600,000. The pesticide preferably also includes a targeting ingredient for directing the active ingredient to a particular target.

21 Claims, 2 Drawing Sheets

(51) Int. Cl.
*A01N 63/02* (2006.01)
*A01N 65/00* (2009.01)
*A01N 65/03* (2009.01)

(56) References Cited

U.S. PATENT DOCUMENTS

| | | | |
|---|---|---|---|
| 4,804,399 | A | 2/1989 | Albrecht |
| 4,865,773 | A | 9/1989 | Kim |
| 5,089,266 | A | 2/1992 | Lee |
| 5,110,804 | A | 5/1992 | Lee |
| 5,366,961 | A | 11/1994 | Harrington |
| 5,391,545 | A | 2/1995 | Pickford |
| 5,432,147 | A * | 7/1995 | Winston et al. ............... 504/101 |
| 5,446,014 | A | 8/1995 | Schuppiser et al. |
| 5,464,805 | A * | 11/1995 | Winston ........................ 504/101 |
| 5,496,568 | A | 3/1996 | Winston |
| 5,518,986 | A | 5/1996 | Winston |
| 5,518,987 | A | 5/1996 | Winston |
| 5,595,749 | A * | 1/1997 | Rascher et al. ............... 424/405 |
| 5,626,858 | A | 5/1997 | Narayanan et al. |
| 5,720,967 | A | 2/1998 | Hall-Hibbitts |
| 5,958,121 | A * | 9/1999 | Lin ............................. 106/31.43 |
| 6,060,429 | A | 5/2000 | Ben-Shalom et al. |
| 6,093,682 | A | 7/2000 | Aren |
| 6,143,312 | A | 11/2000 | Gohbara |
| 6,149,930 | A | 11/2000 | Bonjour |
| 6,699,827 | B2 | 3/2004 | Kim |
| 6,874,421 | B2 * | 4/2005 | Kitchin et al. ................ 101/492 |
| 7,579,017 | B2 * | 8/2009 | Murphy et al. ............... 424/406 |
| 2002/0166147 | A1 | 11/2002 | Jabar, Jr. et al. |
| 2003/0077297 | A1 | 1/2003 | Chen |
| 2003/0072801 | A1 | 4/2003 | Curatolo et al. |
| 2004/0258764 | A1 | 12/2004 | Murphy et al. |
| 2008/0181922 | A1 | 7/2008 | Steckler et al. |

OTHER PUBLICATIONS

International Preliminary Report on Patentability for PCT/US2007/89044, mailed on Jul. 28, 2009, 5 pages.
Pittendrigh, B. R. et al. "Laboratory Evaluations of Xanthan Gum for the Control of Aedes atropalpus (Diptera: Culicidae) Pupae." Environmental Entomology, 1992, vol. 21, No. 6, 4 pages.
International Search Report and Written Opinion of PCT/US2007/89044, mailed on Apr. 29, 2008, 5 pages.

* cited by examiner

Figure 1.

General representation of polysaccharide chains in colloidal micelles.

Figure 2.

Spray droplet encapsulating a whitefly nymph.

PHYSICAL MODE OF ACTION PESTICIDE

This application is a continuation application of U.S. patent application Ser. No. 12/500,051, filed Jul. 9, 2009, currently allowed; which in turn is a continuation application of U.S. patent application Ser. No. 10/463,955, filed Jun. 18, 2003, now U.S. Pat. No. 7,579,017.

BACKGROUND OF THE INVENTION

1. Field of the Invention

The present invention relates to a pesticide with a physical mode of action, containing a low concentration of active ingredient, for use on agricultural plants and soils, which is safer for the environment and humans than traditional pesticides.

2. Description of the Related Art

Insect and fungus induced spoilage of agricultural commodities, such as fruits and vegetables, has been estimated to result in losses of approximately 30% of crops in the United States and up to 50% of crops worldwide.

Agricultural crop losses are primarily caused by insect pest damage and plant diseases. Examples of major crop pests include whiteflies (e.g. *Bemesia tabaci*), mites, aphids and caterpillars that damage crops through direct feeding in fruit and foliage. Insects may also act as vectors of bacterial or viral plant diseases where controlling the insect vector is the only means of preventing infection. Thus, effective agricultural practices to control insect pests and diseases are essential to prevent excessive crop losses.

Conventional agricultural chemical pesticides to control insects and funguses are commonly formulated as solid compositions such as water-dispersible, granular compositions and wettable powder compositions. Conventional solid compositions comprise an active compound, a mineral carrier, and a wetting agent and/or a dispersing agent (see e.g., U.S. Pat. Nos. 6,093,682; 5,595,749; 4,804,399). Pesticide active ingredients are also delivered in solid carriers such as kaolin, chalk, limestone, sodium and potassium alumina silicates, corn meals, sawdust, cellulose powder, activated charcoal and the like. However, such compositions often leave toxic residues which may have an extended impact on humans and the environment.

Hydrocolloids have been used as a delivery system for conventional pesticide active ingredients and are well known in the art. For example, Rascher et al. in U.S. Pat. No. 5,595,749, describes an organophosphate ester active ingredient delivered in a hydrocolloid agent and silicate complex.

Strains of chemical pesticide tolerant insects are increasing at alarming rates, rendering chemical treatments less effective or totally ineffective for agricultural purposes. For this reason, multiple active ingredients are sometimes used simultaneously to improve control of pesticide resistant pest populations. However, this practice often results in a similar decrease in the effectiveness as resistance can also develop rapidly in the pest population against multiple active ingredient pesticides.

Other problems with the use of chemical pesticides are many, including acute and chronic mammalian toxicity, carcinogenicity and other effects on humans and animals that come into contact with them. Moreover, humans who consume produce treated with conventional pesticides and those who are exposed to the environmental conditions they leave behind are at risk. At a time when conventional pesticide use is being restricted and/or eliminated, there is clearly an urgent need to develop new methods of controlling pests, including insects and funguses, that destroy agricultural commodities, which are safer to humans, environmentally benign and effective.

In response to this need, pesticides directed to a physical mode of action rather than a chemical kill have been pursued. However, prior physical kill pesticides have been used with mixed success. Their use of ingredients in high concentrations leads to various problems such as clogging of spray equipment, uneven and problematic application and reduced efficiency of application machinery. Significantly, the use of existing physical kill pesticides has also been associated with crop damage from the high concentrations of the physical control active ingredients used in these compositions.

Accordingly, there is a need in the art for a pesticide to effectively control insects and funguses that cause loss of agricultural commodities, such as fruits, vegetables, fiber and flowers. There is a further need for pesticides that are safer for workers, consumers and the environment and can be delivered efficiently and effectively in an aqueous form.

SUMMARY OF THE INVENTION

The present invention relates to a pesticide for application on plants or soils, delivering a physical mode of action kill that is effective at low concentrations of the active ingredient. The present invention further includes methods for the manufacture and application of such a pesticide. More particularly, the present invention is directed to a pesticide for delivering a physical mode of action kill, comprising a polymer active ingredient in a concentration of less than 0.10 wt. %, a surfactant, a co-solvent and a diluent, wherein the polymer is in the form of micelles in a colloid suspension.

The composition of the invention comprises a polymer in low concentrations, as the active ingredient, capable of being formed into a hydrocolloid suspension. The preferred polymers contemplated for use in the present invention are long chain polysaccharides, considered as those having 10 or more monosaccharide units and a molecular weight in the range of about 10,000 to about 25,000,000 and most preferably in the range of about 600,000. Further, the use of various blends of polysaccharides, for example, alginate and starch may be desirable.

However, the invention is not limited to the use of one particular type of polymer or polysaccharide active ingredient, and may include the use of other compounds, with a particle size in the range of 1-100 nm (nanometers). Examples of other compounds include enzymes; amino acids; polypeptides; proteins; or other large molecules and particles, which may be included for various purposes described below.

The hydrocolloid suspension is comprised of dispersions of polymer particles that form discrete units or micelles (e.g. shell-like structure) intimately distributed within the molecules of a diluent. The colloidal suspension is preferably formed with an aqueous diluent, preferably water. The preferred hydrocolloid distribution consists of polysaccharide micelles smaller than 1.0 um (micron) that are suspended by Brownian motion in solution.

The micelles of the hydrocolloid suspension are molecular aggregates of polymer particles, preferably polysaccharide particles, and tend to become charged by adsorption of ions from the diluent, or by ionization of functional groups on the surface of the polymers.

The hydrocolloid suspension also preferably contains co-solvents and a surfactant. Preferably, at least one co-solvent, a surfactant and optionally a color additive are used with the polymer in the diluent to form a low toxicity, physical kill mode of action pesticide, which effectively controls insects and funguses found on plants and in the soil.

The surfactant in the aqueous solution of the hydrocolloid suspension acts as an interfacial stabilizer between the surfaces of the polysaccharide micelles and molecules of the diluent. The surfactant's effect on the surfaces of the hydrocolloid molecules and particles enhances the distribution of the low concentration of active ingredient throughout the hydrocolloid suspension.

Additionally, the surfactant decreases the surface tension present on the plant surface and the insect cuticle. This effect enhances spray coverage on the leaf surface in spite of the hydrophobic nature of the leaf and insect exoskeleton.

Without limiting the invention, it is believed that once the hydrocolloid suspension is applied, the micelles of active ingredient begin to attach themselves in large numbers to the plant and insect cuticle. As the suspension begins to evaporate, a compressed layer of polymer is left behind, effectively blocking the trachea, spiracles and transpiration across the remainder of the insect cuticle. The insect dies within a few hours and desiccation makes the effect readily apparent within a day or two.

Moreover, the polymer active ingredient can be positively, negatively or neutrally charged with a targeting ingredient, that may also include receptor specific compounds that work at the molecular level to perform specific tasks. In particular, the hydrocolloid suspension can be programmed for attraction or deterrence to specific plants, insects or fungi, or for enhanced penetration of surrounding plant soil.

The targeting ingredient added to the composition is preferably one or more elements and/or compounds which provide an affinity to a particular target of the active ingredient. In one example, the targeting ingredient can be positively or negatively charged, depending on what the target is, and lends its charge to the micelles of the polysaccharide active ingredient. In this example, the targeting ingredient programs the active ingredient to selectively adhere to oppositely charged targets, between the plant and insect.

The use of a targeting ingredient thereby increases the effectiveness and decreases the amount of the active ingredient necessary to perform its insecticidal/fungicidal activity. As such, in the above example, a significant negative ionic charge attached to the polysaccharide micelles with a targeting ingredient, such as potassium phosphate, promotes greater attraction of micelles to the insect cuticle relative to the leaf surface, thereby increasing the amount of active ingredient on and around the insect. Conversely, reducing the negative charge tends to promote greater attraction to the leaf surface, useful when the pesticide functions as a fungicide.

The use of deionized water as the diluent for the colloid suspension is especially preferred when an ionic compound is used as the targeting ingredient. In this regard, the deionized water enhances the effectiveness of the ionically active hydrocolloid suspension.

The targeting ingredient is not limited to positively and negatively charged ionic components, and contemplates the use of various elements and/or compounds that interact with receptor sites found on plant and insect surfaces. When attached to the polymer or polysaccharide active ingredient, the receptor specific targeting ingredient attaches to specific receptor sites located in or around the insect cuticle. As such, the active ingredient may be effectively deposited in a designated area, effectively blocking the trachea, spiracles and transpiration across the remainder of the insect cuticle.

The receptor specific targeting ingredient can be of such a nature as to selectively attach to receptors located on insects, funguses or plants or a combination thereof, if so desired. In particular, the presently claimed insecticide may be programmed to selectively attach to specific insects, plants or funguses through the use of targeting ingredients having various ionic properties, receptor interactions and/or binding capabilities.

In this regard, the invention includes surface-introduction of nanometer sized features such as ionic charges and receptor site binding compounds, and methods for the controlled derivation of the active ingredient in contact with insects, plants and other biological macromolecules. Contemplated is the optimal binding of targeting ingredients to functional biomolecules while minimizing non-specific adsorption in areas of unimportance.

Thus, the preferred embodiment of the present invention involves the manipulation of hydrocolloidal particles through the use of targeting ingredients to interact with model substrates for surface modification. It aims at analytical techniques for accurate assessment in the targeting of colloid suspension polymer particles by means of positive, negative or neutral charges and/or receptor site specific association of the colloidal suspension for its use as a physical-kill pesticide.

The invention also functions in its intended manner when introduced into the surroundings plant soil. Specifically, the composition can be used not only for its pesticide function but also to enhance plant growth and production by improving soil conditions, providing nutrient sources and decreasing fungus and insect infestations.

BRIEF DESCRIPTION OF THE DRAWINGS

The following drawings are included for illustration of the present invention without limiting the invention in any manner whatsoever, wherein:

FIG. 1 depicts a general representation of anionic high molecular weight polysaccharide chains in colloidal micelles.

FIG. 2 depicts an enlarged area of a treated plant leaf showing spray droplets surrounding and enveloping a whitefly nymph.

DETAILED DESCRIPTION OF THE PREFERRED EMBODIMENT

Figure 3:
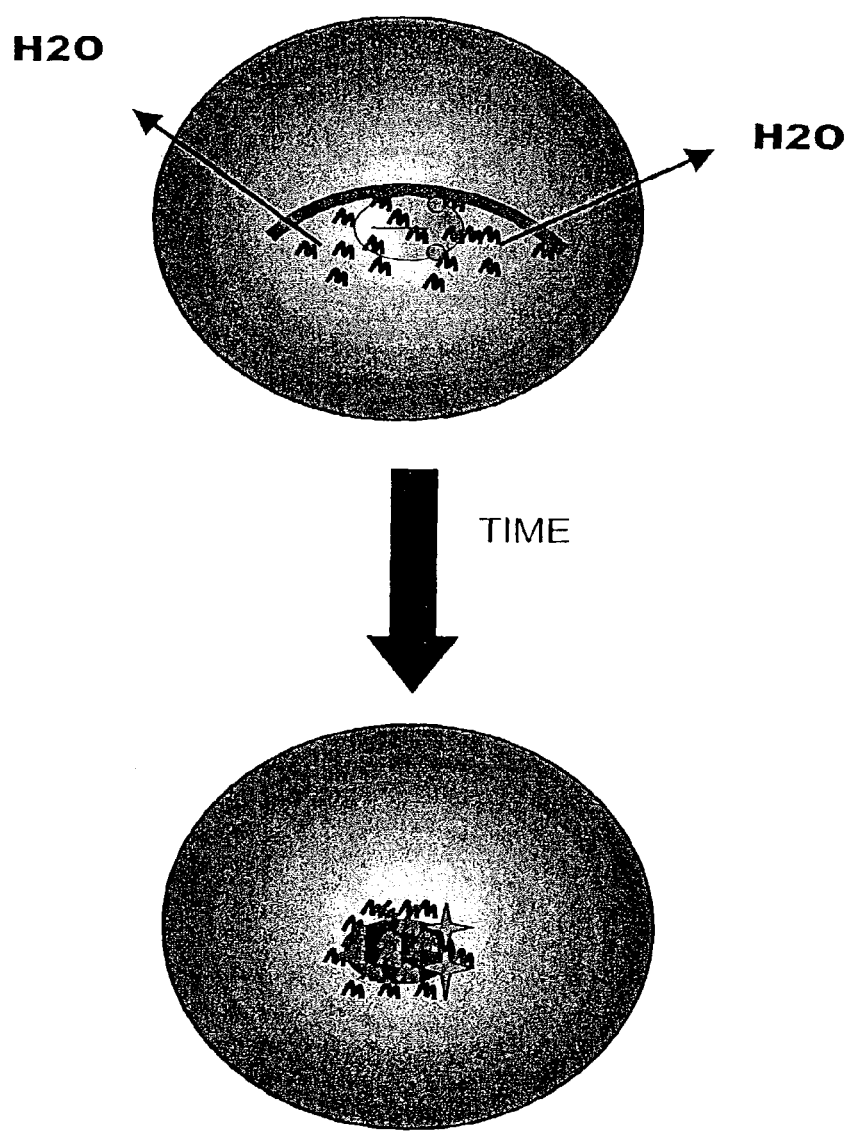
FIG. 3 depicts an insect enveloped by a compressed layer of polysaccharide gum after evaporation of the hydrocolloid suspension.

The present invention is directed to a pesticide for delivering a physical mode of action kill comprising a polymer active ingredient in a concentration of less than 0.10 wt. %, a surfactant, a co-solvent, and a diluent, wherein the polymer is in the form of micelles in a colloid suspension. In this regard, the polymer can he any polymer that can be formed into a colloid suspension and works as an active ingredient in the physical mode of operation killing of insects and funguses.

The preferred embodiment comprises an active, low toxicity, biodegradable, environmentally and mammalian safe insecticidal and fungicidal hydrocolloid suspension which can be sprayed safely on all agricultural plants and soils. The pesticide of the preferred embodiment comprises a very low concentration of high molecular weight polysaccharide, a surfactant, a co-solvent, a diluent, and preferably a targeting ingredient, that may be ionically charged or receptor site specific, in a hydrocolloid suspension.

The term long chain or high molecular weight polysaccharide as used in the specification and claims is defined as a carbohydrate containing 10 or more monosaccharide units linked together, having a molecular weight of about 10,000 to 25,000,000, and a particle size less than 1 micron.

Polysaccharides suitable for use in the present invention include, but are not limited to, xanthan gum, alginate gum, alginic acid, propylene glycol alginate, starches such as corn starch, potato starch, rice starch, tapioca starch and wheat starch; modified starches such as dextrins; genetically modified starches such as corn starches comprising 100% amylopectin, or a mixture of amylopectin and amylose (such as 50% amylopectin and 50% amylose or 30% amylopectin and 70% amylose); glycogen; agar; pectin; carrageenan; and natural gums such as arabic gum, guar gum, karaya gum and tragacanth gum; and mixtures thereof.

The preferred polysaccharides of this invention comprise high molecular weight polysaccharides such as xanthan gum and alginate gum. The most preferred high molecular weight polysaccharides of the present invention are xanthan gum and alginate having a molecular weight of about 10,000 to 600,000.

It is anticipated that the pesticide will be formed as a concentrate, which is then diluted for application by 1:50 to 1:1000, and preferably, 1:100 to 1:300. Surprisingly, and not previously demonstrated, it has been found that very low concentrations, in the range of about 0.00001 to 1.0 wt. %, of the high molecular weight polysaccharides in a hydrocolloid suspension, with a targeting component and a diluent, are effective physical kill insecticides and fungicides. The preferred concentration of the high molecular weight polysaccharides in the diluent is in the range of about 0.001 to 0.09 weight %, with the most preferred concentration of the high molecular weight polysaccharides being in the range of about 0.06 weight %.

The preferred polysaccharide micelles are smaller than 1.0 um (micron), and are suspended in the aqueous solution by Brownian motion. The hydrocolloidal properties maintain a homogeneous distribution of the polysaccharide that does not settle out over time.

Targeting ingredients as used in the specification and claims are defined as elements and/or compounds capable of mixing with or combining with the polysaccharide hydrocolloid micelles to provide an affinity to a particular target. As such, the targeting ingredients provide for a selective delivery system.

As currently contemplated, without limitation, targeting ingredients may be ionic or non-ionic salts, esters, amino acids, peptides, proteins and other natural or synthetic compounds that can direct or manipulate the polysaccharides as desired. Although any suitable ionically charged targeting ingredient can be used, the most preferred ionically charged targeting ingredient is potassium phosphate, with monopotassium phosphate or potassium dihydrogen phosphate being most preferred, for use with the preferred high molecular weight polysaccharide active ingredient.

In the most preferred embodiment, the preferred ionic monopotassium phosphate or potassium dihydrogen phosphate and high molecular weight polysaccharide are combined in ratios of about 30:1 to 5:1, preferably about 25:1 to 10:1 and more preferably about 15:1, to form ionically charged micelles. It is believed, without limitation, that the aqueous dispersions of micelles attach to the bodies of the insects in large numbers, enhanced by the ionic charge on the polysaccharide micelles. Upon evaporation, a compressed layer of polysaccharide envelops the organism causing its desiccation and death.

The surfactant is used in the formula to promote distribution of the hydrocolloid suspension, and decrease the surface tension present on both the leaf surface and the insect cuticle. The surfactant action maximizes spray coverage on the leaf surface in spite of the hydrophobic nature of the leaf and insect exoskeleton. Further, when ionically charged, the high molecular weight polysaccharide micelles have a greater attraction to the insect exoskeleton rather than the leaf surface. This attraction causes the active ingredients to gather around and adhere to the insect body, enhancing effectiveness.

Surfactants suitable for use in the present invention may comprise conventional surfactants such as anionic and nonionic surfactants. Preferred are anionic surfactants such as salts of fatty acids, alkyl sulphates, alkyl ether sulphonates and alkyl aryl sulphonates.

Examples of more preferable surfactants include polyoxyethelene dodecylphenol, sodium laurel sulfate, ethoxylated phenols, dodecylphenol ethoxylate, alkyl benzene sulfonic acid, sodium olefin sulfonate, sodium laurel ethoxy sulphate, linear alcohol exthoxylate such as lauryl alcohol ethoxylate, alkane sulphonate and alkyl sulphonic acid. The most preferred surfactants are polyoxyethelene dodecylphenol and dodecylphenol ethoxylate.

When the given components cannot be formed into a miscible composition, a co-solvent may be used to provide a miscible composition. The preferred co-solvent is generally a glycol or an ester of a straight or branched-chain alcohol. For instance, glycol ether may be added as a co-solvent in an amount effective to solubilize the components of the mixture.

Non-limiting examples of representative classes of such other co-solvents include hydrocarbons, ethers, phenols, glycols, lactones, chlorinated hydrocarbons, aromatic hydrocarbons nitrated hydrocarbons, dibasic esters, mono-esters such as ethyl acetate, butyl acetate, ethyl-3-ethoxy-propionate, propylene glycol propanediol, propylene glycol butyl ether acetate, dipropylene glycol methyl ether acetate and tetrahydrofurfuryl alcohol. The most preferred co-solvents are propylene glycol (propanediol) and tetrahydrofurfuryl alcohol.

The amount of co-solvents used may vary depending on the specific composition of interest, as one of skill in the art may appreciate. The particular type and amount of co-solvent which will afford a miscible composition may be identified by routine experimentation.

The non-toxic aqueous insecticide may also contain various additives such as antioxidants, preservatives, coloring agents, pH neutralizers and/or clarifiers, such as those generally known in the art.

Examples of suitable antioxidants are hexamethylene tetramine, tetramethyl thiuram monosulfide, paratoluidine, phenyl beta naphthylamine and triethyl trimethyl triamine, ammonium nitrate and sodium nitrate and synthetic and natural resins such as wood rosin and phenol formaldehyde.

Some examples of suitable preservatives are sodium silicate, sodium dehydroacetate and sodium benzoate, bromonitro propane diods such as 2-bromopropane 1,3-diol, 3-iodo-2-propylbutyl carbamate; and benzothiazolin-2-one, which may be added as a preservative to inhibit microorganism growth and may be incorporated during formation of the composition of this invention.

Examples of some preferred buffering agents, when used, include potassium hydroxide, ammonium bicarbonate, ammonium phosphate dibasic, and diammonium phosphate.

Additionally, examples of a neutralizer and a coloring agent which have been found to be suitable, without limitation, are potassium hydroxide and caramel color, respectively.

The balance of the non-toxic pesticide is a diluent, comprising one or more diluents. Due to the ionic nature of the active ingredient, it is preferred that deionized water be used as the diluent for the present pesticide.

In use, the non-toxic aqueous pesticide dilution is sprayed or misted on the plant or soil, to directly contact the surface of the target pests. When so applied, the low toxicity aqueous pesticide is effective in controlling various plant pests and pathogens, including, but not limited to, fungi, whiteflies, mites, aphides and the like. Since the mechanism of insect and mite control with the presently claimed invention is by suffocation and/or repellency of male and of egg laying females, there is no requirement for the addition of toxic chemicals. As such, the instant invention provides a virtually non-toxic alternative to broad spectrum insecticides. In some cases, repeated applications may be required.

In the preferred embodiment, stable colloid suspension pesticides preferably comprise on a weight to weight basis about 0.5% to 2.0% of potassium dihydrogen phosphate or potassium monophosphate compounds or a similar ionically charged compounds; about 40% to 65% of deionized water; about 20% to 40% of a surfactant; about 10% to 25% of a co-solvent; about 0.0001% to 0.1% of an anionic high molecular weight polysaccharide; 0.01% to about 1.0% of a neutralizing agent; and optionally, about 0% to 0.08% of a coloring agent.

The more preferred colloid suspension pesticides of this invention preferably comprise on a weight to weight basis about 0.9% to 1.1% of potassium dihydrogen phosphate or potassium monophosphate compounds; about 47% to 58% of deionized water; about 27% to 33% of a surfactant; about 15% to 20% of a co-solvent; about 0.001% to 0.1% of an anionic high molecular weight polysaccharide; 0.01% to about 0.5% of a neutralizing agent; and optionally about 0% to 0.04% of a coloring agent.

In order to facilitate a further understanding of this invention, the following examples are presented primarily for the purpose of illustrating more specific details thereof. The invention should not be deemed limited thereby, except as defined in the appended claims.

EXAMPLE 1

Ingredients:
Potassium dihydrogen phosphate (83.7 lbs., 0.98 wt. %) Ashland Distribution & Chemical Group, Ashland Inc., Columbus, Ohio; deionized water (4404 lbs., 51.95 wt. %); polyoxyethelene dodecylphenol (2595.5 lbs., 30.4 wt %) as T-DET DD7, Harcros Organics, Kansas City, Kans.; tetrahydrofurfuryl alcohol (1314.8 lbs., 15.4 wt. %), THFA manufactured by Ashland Distribution & Chemical Group, Ashland Inc., Columbus, Ohio; propylene glycol propanediol (117.0 lbs., 1.37 wt. %) manufactured by Ashland Distribution & Chemical Group, Ashland Inc., Columbus, Ohio; xanthan gum (5.1 lbs., 0.06 wt. %) Keltrol®, C.P. Kelco, San Diego Calif.; potassium hydroxide (caustic potash, 13.7 lbs., 0.16 wt. %), Ashland Distribution & Chemical Group, Ashland Inc., Columbus, Ohio; caramel color (3.4 lbs., 0.04 wt. %), D.D. Williamson & Co. Inc., Columbus Ohio.

Potassium Phosphate Premix:
Add one half of the total water (deionized water, total is 4404.7 lbs., 51.6 wt. %) to a mixing tank, and while the agitation and recirculation is on, add potassium phosphate (potassium dihydrogen phosphate total is 83.7 lbs., 0.98 wt. %, manufactured by Ashland Distribution & Chemical Group, Ashland Inc., Columbus, Ohio). Once the potassium phosphate is dissolved, a sample is removed and analyzed. If sample passes analysis, this batch of premix is ready for production.

Xanthan Gum Premix:
The remaining water (one half total) is place in a separate tank. The xanthan gum (total of 5.1 lbs., 0.06 wt. %, Keltrol®, C. P. Kelco, San Diego Calif.) is sprinkled into the propylene glycol (propylene glycol propanediol, total of 117.0 lbs., 1.37 wt. %, manufactured by Ashland Distribution & Chemical Group, Ashland Inc., Columbus, Ohio), once mixed it is immediately added to the water to prevent gelling. Next, the mixture is gently stirred with a paddle and not a propeller to avoid encapsulating air and making bubbles in the mixture, which are difficult to remove.

The mixture is then left to sit for approximately 6 to 24 hours before use.

Formula Mix:
The polyoxyethelene dodecylphenol (total of 2595.5 lbs., 30.4 wt. %) as T-DET DD7, Harcros Organics, Kansas City, Kans.) is warmed to room temperature to ensure the material is completely liquefied. Only full drums of the T-DET DD7, never partial drums, are to be used. In a clean tank, the potassium phosphate premix and warm xanthan premix are added and mixed until solution is uniform. In a separate tank, add the tetrahydrofurfuryl alcohol (total of 1314.8 lbs., 15.4 wt. %, THFA manufactured by Ashland Distribution & Chemical Group, Ashland Inc., Columbus, Ohio) co-solvent followed by warm polyoxyethelene dodecylphenol (total of 2595.5 lbs., 30.4 wt. %, T-DET DD7, Harcros Organics, Kansas City, Kans.), and mix until uniform. The solution is pumped slowly into the tank containing the potassium phosphate and xanthan gum premixes. Using a diaphragm pump and paddle agitation only, once the mix is uniform, a sample for analysis is taken. Ensure the temperature of the solution and the solutions clarity is monitored following the quality assurance guidelines. Of particular note, if the mixing of solutions is too rapid or improper the entire mix may turn into gel. Also, a very stable foam can also be created upon rapid mixing of the solutions.

After 4 to 8 hours, add sufficient potassium hydroxide (caustic potash, 13.7 lbs., 0.16 wt. %, Ashland Distribution & Chemical Group, Ashland Inc., Columbus, Ohio) to raise the PH of the solution to 7.0. Add caramel coloring (total of 3.4 lbs., 0.04 wt. %, D.D. Williamson & Co. Inc., Columbus Ohio), and paddle agitate the solution until uniform.

EXAMPLE 2

Ingredients:
Propylene glycol alginate (0.078 wt. %, Kelcoloid HVF®, manufactured by ISP Alginates); deionized water (51.59 wt. %, manufactured by Acropure); dodecylphenol ethoxylate (30.40 wt. %, T-DET DD7, manufactured by Harcros Organics); tetrahydrofurfuryl alcohol (15.40 wt. %, THFA manufactured by Ashland Distribution & Chemical Group, Ashland Inc., Columbus, Ohio); propylene glycol propanediol (1.37 wt. %, manufactured by Ashland Distribution & Chemical Group, Ashland Inc., Columbus, Ohio); potassium phosphate (0.98 wt. %, Europhos MKP FG®, Ashland Distribution & Chemical Group, Ashland Inc., Columbus, Ohio); potassium hydroxide (caustic potash, 0.083 wt. %, Ashland Distribution & Chemical Group, Ashland Inc., Columbus, Ohio); caramel color (0.04 wt. %, D.D. Williamson & Co. Inc., Columbus Ohio); xanthan gum (0.01 wt. %, Keltrol®, C.P. Kelco, San Diego Calif.).

Potassium Phosphate Premix:
Add one half of the total deionized water, 51.59 wt. %. to a mixing tank, and while the agitation and recirculation is on add potassium phosphate, 0.98 wt. %., Europhos MKP FG®, Ashland Distribution & Chemical Group, Ashland Inc., Columbus, Ohio. Once the potassium phosphate is dissolved, a sample is removed and analyzed. If sample passes analysis, this batch of premix is ready for production.

Xanthan Gum and Propylene Glycol Alginate Premix:

The remaining water (one half total) is place in a separate tank. The xanthan gum, 0.01 wt. %, Ketrol®, C. P. Kelco, San Diego Calif., is mixed with the propylene glycol alginate 0.078 wt. %, Kelcoloid HVF® and sprinkled into the propylene glycol propanediol, 1.37 wt. %, manufactured by Ashland Distribution & Chemical Group, Ashland Inc., Columbus, Ohio, once mixed it is immediately added to the water to prevent gelling. Next, the mixture is gently stirred with a paddle and not a propeller to avoid encapsulating air and making bubbles in the mixture, which are difficult to remove.

The mixture is then left to sit for approximately 6 to 24 hours before use.

Formula Mix:

The dodecylphenol ethoxylate, 30.40 wt. %) as T-DET DD7, Harcros Organics, Kansas City, Kans. is warmed to room temperature to ensure the material is completely liquefied. In a clean tank, the potassium phosphate premix and warm xanthan/propylene glycol alginate premix are added and mixed until solution is uniform. In a separate tank, add the tetrahydrofurfuryl alcohol, 15.40 wt. %, THFA manufactured by Ashland Distribution & Chemical Group, Ashland Inc., Columbus, Ohio, and mix until uniform. The solution is pumped slowly into the tank containing the potassium phosphate and xanthan/propylene glycol alginate gum premixes. Using a diaphragm pump and paddle agitation only, once the mix is uniform, a sample for analysis is taken. Ensure the temperature of the solution and the solutions clarity is monitored following the quality assurance guidelines. Of particular note, if the mixing of solutions is too rapid or improper the entire mix may turn into gel. Also, a very stable foam can also be created upon rapid mixing of the solutions.

After 4 to 8 hours, add sufficient potassium hydroxide, 0.083 wt. %, Ashland Distribution & Chemical Group, Ashland Inc., Columbus, Ohio, to raise the PH of the solution to 7.0. Add caramel coloring, 0.04 wt. %, D.D. Williamson & Co. Inc., Columbus Ohio, and paddle agitate the solution until uniform.

The invention accordingly comprises the features of construction, combination of elements, and arrangement of elements which are exemplified, without limitation, herein. The scope of the invention will be limited solely by the appended. All patents cited are hereby incorporated by reference.

The invention claimed is:

1. A mammalian safe, low-toxicity pesticide for delivering a physical mode of action kill comprising:
(a) a mammalian safe, low-toxicity active ingredient comprising a polysaccharide selected from the group consisting of xanthan gum, alginate gum, alginic acid, propylene glycol alginate, starches, dextrins, corn starches comprising 100% amylopectin, corn starches comprising a mixture of amylopectin and amylose, glycogen, agar, pectin, carrageenan, other natural gums and combinations thereof, said active ingredient being present in a concentration of less than 0.10 wt. %;
(b) about 20 wt. % to about 40 wt. % of a mammalian safe, low-toxicity surfactant selected from the group consisting of polyoxvethylene dodecvlphenol, dodecvlphenol ethoxvlate, sodium dodecvlbenzene sulphonate, ethoxvlate phenol, sodium laurvl sulphate, sodium olefin sulfonate, sodium lauryl ethoxy sulphate, linear alcohol ethoxylate, alkane sulphonate and mixtures thereof;
(c) about 10 wt. % to about 25 wt. % of a mammalian safe, low-toxicity co-solvent selected from the group consisting of glycols, esters of straight-chain alcohols, esters of branched-chain alcohols, hydrocarbons, ethers, phenols, glycols, lactones, nitrated hydrocarbons, dibasic esters, ethyl acetate, butyl acetate, ethyl-3-ethoxy-propionate, propylene glycol propanediol, propylene glycol butyl ether acetate, dipropylene glycol methyl ether acetate, tetrahydrofurfuryl alcohol and combinations thereof;
(d) about 40 wt. % to about 65 wt. % of a diluent comprising water;
(e) about 0.5 wt. % to about 2.0 wt. % of a mammalian safe, low-toxicity pest targeting ingredient selected from the group consisting of ionic salts, non-ionic salts, esters, amino acids, peptides, proteins and combinations thereof, said pest targeting ingredient being able to increase the effectiveness of said active ingredient;
(f) optionally about 0 wt. % to about 0.05 wt. % of a mammalian safe, low-toxicity coloring agent; and
(g) optionally about 0.01 wt. % to about 1.0 wt. % of a mammalian safe, low-toxicity buffering agent selected from the group consisting of potassium hydroxide, ammonium bicarbonate, ammonium phosphate dibasic, diammonium phosphate and combinations thereof;

wherein said polysaccharide is in the form of a micelle in a colloid suspension and is present in an amount sufficient to cause a physical mode of action kill in pests, wherein said wt. % is based on the total weight of said pesticide;

with the proviso that no other pesticidally active ingredient is present in the pesticide.

2. The mammalian safe, low-toxicity pesticide of claim 1 wherein said polysaccharide has a molecular weight of about 10,000 to 25,000,000.

3. The mammalian safe, low-toxicity pesticide of claim 1 wherein the polysaccharide is selected from the group consisting of xanthan gum, alginic acid, propylene glycol alginate, starch, carrageenan and natural gums.

4. The mammalian safe, low-toxicity pesticide of claim 3 wherein the polysaccharide is xanthan gum.

5. The mammalian safe, low-toxicity pesticide of claim 1 wherein the concentration of the polysaccharide is in the range of from about 0.00001 to 0.09 wt. %.

6. The mammalian safe, low-toxicity pesticide of claim 5 wherein the polysaccharide is in a concentration of from about 0.001 to about 0.06 wt. %.

7. The mammalian safe, low-toxicity pesticide of claim 1 wherein the mammalian safe, low-toxicity pest targeting ingredient is potassium phosphate.

8. The mammalian safe, low-toxicity pesticide of claim 7 wherein the mammalian safe, low-toxicity pest targeting ingredient is selected from the group consisting of monopotassium phosphate, potassium dihydrogen phosphate and mixtures thereof.

9. The mammalian safe, low-toxicity pesticide of claim 1 wherein the ratio of mammalian safe, low-toxicity pest targeting ingredient to polysaccharide is from about 30:1 to about 5:1.

10. The mammalian safe, low-toxicity pesticide of claim 9 wherein the ratio of mammalian safe, low-toxicity pest targeting ingredient to polysaccharide is from about 20:1 to about 10:1.

11. The mammalian safe, low-toxicity pesticide of claim 9 wherein the ratio of mammalian safe, low-toxicity pest targeting ingredient to polysaccharide is about 15:1.

12. The mammalian safe, low-toxicity pesticide of claim 1 wherein said mammalian safe, low-toxicity surfactant is polyoxyethelene dodecylphenol.

13. The mammalian safe, low-toxicity pesticide of claim 1 wherein said mammalian safe, low-toxicity co-solvent is selected from the group consisting of glycols, lactones, chlorinated hdrocarbons, dibasic esters, ethyl-3-ethoxy-propionate, propylene glycol propanediol, propylene glycol butyl ether acetate, dipropylene glycol methyl ether acetate, tetrahydrofurfuryl alcohol and mixtures thereof.

14. The mammalian safe, low-toxicity pesticide of claim 13 wherein said mammalian safe, low-toxicity co-solvent is selected from the group consisting of tetrahydrofurfuryl alcohol, propylene glycol propanediol and combinations thereof.

15. The mammalian safe, low-toxicity pesticide of claim 1 wherein the mammalian safe, low-toxicity coloring agent, when present, is caramel color.

16. The mammalian safe, low-toxicity pesticide of claim 1 wherein the mammalian safe, low-toxicity pesticide comprises
    from about 0.9 wt. % to about 1.1 wt. % of the mammalian safe, low-toxicity pest targeting ingredient;
    from about 47 wt. % to about 58 wt. % of the diluent;
    from about 27 wt. % to about 33 wt. % of the mammalian safe, low-toxicity surfactant;
    from about 15 wt. % to about 20 wt. % of the mammalian safe, low-toxicity co-solvent;
    from about 0.0001 wt. % to about 0.09 wt. % of the polysaccharide;
    from about 0.01 wt. % to about 0.5 wt. % of the mammalian safe, low-toxicity buffering agent; and
    optionally, from about 0 wt. % to about 0.04 wt. % of the coloring agent.

17. The mammalian safe, low-toxicity pesticide of claim 1 wherein the diluent is deionized water.

18. A method of killing pests on plants by physical mode of operation comprising the step of applying to the locus of the pest a pesticidally effective amount of a mammalian safe, low-toxicity pesticide as described in claim 1.

19. A process for the preparation of the mammalian safe, low-toxicity pesticide of claim 1 comprising forming a colloid suspension comprising a polysaccharide in a concentration of less than 0.10 wt. % and a mammalian safe, low-toxicity pest targeting ingredient.

20. The mammalian safe, low-toxicity pesticide of claim 9 wherein the ratio of mammalian safe, low-toxicity pest targeting ingredient to polysaccharide is from about 25:1 to about 10:1.

21. The mammalian safe, low-toxicity pesticide of claim 1 wherein the mammalian safe, low-toxicity starch is selected from the group consisting of corn starch, potato starch, rice starch, tapioca starch, wheat starch and combinations thereof.

* * * * *

UNITED STATES PATENT AND TRADEMARK OFFICE
CERTIFICATE OF CORRECTION

Page 1 of 1

PATENT NO. : 9,107,409 B2
APPLICATION NO. : 13/628625
DATED : August 18, 2015
INVENTOR(S) : Brook Chandler Murphy and Todd C. Steckler It is certified that error appears in the above-identified patent and that said Letters Patent is hereby corrected as shown below:

Claims

In Claim 1 at column 9, lines 61, delete "polyoxvethylene dodecvlphenol, dodecvlphenol ethoxvlate, sodium dodecvlbenzene sulphonate, ethoxvlate phenol, sodium laurvl sulphate" and insert --polyoxyethylene dodecylphenol, dodecylphenol ethoxylate, sodium dodecylbenzene sulphonate, ethoxylate phenol, sodium lauryl sulphate--.

In Claim 13 at column 11, line 4, delete "hdrocarbons" and insert --hydrocarbons--.

Signed and Sealed this
Ninth Day of February, 2016

Michelle K. Lee
*Director of the United States Patent and Trademark Office*